US010429372B2

(12) United States Patent
Al-Yousef et al.

(10) Patent No.: US 10,429,372 B2
(45) Date of Patent: *Oct. 1, 2019

(54) SMART WATER FLOODING PROCESSES FOR INCREASING HYDROCARBON RECOVERY

(71) Applicant: Saudi Arabian Oil Company, Dhahran (SA)

(72) Inventors: Ali Al-Yousef, Dhahran (SA); Subhash Ayirala, Katy, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,131

(22) Filed: May 11, 2018

(65) Prior Publication Data

US 2018/0259499 A1    Sep. 13, 2018

Related U.S. Application Data

(63) Continuation-in-part of application No. 15/209,597, filed on Jul. 13, 2016, now Pat. No. 10,000,687.

(Continued)

(51) Int. Cl.
   *E21B 49/00* (2006.01)
   *G01N 33/28* (2006.01)
   (Continued)

(52) U.S. Cl.
   CPC ......... *G01N 33/2847* (2013.01); *E21B 43/20* (2013.01); *G01N 11/02* (2013.01); *G01N 13/02* (2013.01); *G01N 15/08* (2013.01)

(58) Field of Classification Search
   CPC . C09K 8/58; C09K 8/584; C09K 8/80; C09K 8/905; G01N 33/2823;
   (Continued)

(56) References Cited

U.S. PATENT DOCUMENTS 8,191,416 B2   6/2012   Kuchuk et al.
8,550,164 B2   10/2013  Al-Yousef et al.
(Continued)

FOREIGN PATENT DOCUMENTS

WO    2013091023 A2    6/2013
WO    2013156866 A2    10/2013

OTHER PUBLICATIONS

Kumar, et al., "Atomic Force Microscopy Study of Wettability Alteration," SPE International Symposium on Oilfield Chemistry, The Woodlands, TX, Feb. 2005.
(Continued)

*Primary Examiner* — Harshad R Patel
*Assistant Examiner* — Nigel H Plumb
(74) *Attorney, Agent, or Firm* — Bracewell LLP; Constance G. Rhebergen; Kevin R. Tamm

(57) ABSTRACT

A method for measuring liquid-rock and liquid-liquid interfaces including performing at least one measurement technique proximate a subterranean rock sample and an interfacial liquid hydrocarbon fraction, where a liquid hydrocarbon fraction and the subterranean rock sample are combined to exhibit a first interface between the liquid hydrocarbon fraction and the subterranean rock sample, producing the interfacial liquid hydrocarbon fraction. The method includes performing at least one measurement technique proximate the interfacial liquid hydrocarbon fraction and a brine solution, where the liquid hydrocarbon fraction and the brine solution are combined to exhibit a second interface between the liquid hydrocarbon fraction and the brine solution, and where the measurement techniques result in measurements of the interfacial liquid hydrocarbon fraction at macro, micro to nano, nano to sub-nano, and sub-nano scales, and result in measurements of the second interface at macro and micro to nano scales.

20 Claims, 2 Drawing Sheets

Related U.S. Application Data

(60) Provisional application No. 62/193,951, filed on Jul. 17, 2015.

(51) Int. Cl.
    *G01N 11/02* (2006.01)
    *G01N 15/08* (2006.01)
    *G01N 13/02* (2006.01)
    *E21B 43/20* (2006.01)

(58) Field of Classification Search
    CPC ...... G01N 33/2847; G01N 7/14; G01N 33/18; G01N 11/02; G01N 13/02; G01N 15/08; E21B 49/081; E21B 49/00; E21B 49/10; E21B 47/1015; E21B 1/00; E21B 43/20; G01P 13/02; G01F 1/50
    See application file for complete search history.

(56) References Cited

U.S. PATENT DOCUMENTS

| | | | |
|---|---|---|---|
| 8,776,880 B2 | 7/2014 | Pich et al. | |
| 8,973,660 B2 | 3/2015 | DiFoggio | |
| 10,000,687 B2 * | 6/2018 | Al-Yousef | C09K 8/58 |
| 2002/0035040 A1 * | 3/2002 | Talashek | C09K 8/08 |
| | | | 507/200 |
| 2012/0157358 A1 | 6/2012 | Fang et al. | |
| 2013/0125630 A1 | 5/2013 | Collins et al. | |
| 2013/0274149 A1 | 10/2013 | Lafitte et al. | |
| 2015/0096746 A1 | 4/2015 | DiFoggio et al. | |
| 2017/0015893 A1 | 1/2017 | Al-Yousef et al. | |

OTHER PUBLICATIONS

Hassenkam, et al., "A Fast Alternative to Core Plug Tests for Optimising Injection Water Salinity for EOR," SPE Improved Oil Recovery Symposium, Tulsa, OK, Apr. 2014.

Al-Yousef, et al., "Laboratory Investigation of the Impact of Injection-Water Salinity and Ionic Content on Oil Recovery From Carbonate Reservoirs," SPE Improved Oil Recovery Symposium, Tulsa, OK, Apr. 2012.

Al-Yousef, et al., "Improved/Enhanced Oil Recovery From Carbonate Reservoirs by Tuning Injection Water Salinity and Ionic Content," SPE Reservoir Evaluation & Engineering, Oct. 2011, pp. 578-593.

Schmatz et al., "Nanosccale imaging of pore-scale fluid-fluid-solid contacts in sandstone", AGU Publications, 2015, pp. 2189-2195, The Authors.

Yousef et al., "Laboratory investigating of Novel Oil Recovery Method for Carbonate Reservoirs", Canadian Society for Unconventional Gas, 2010, pp. 1-35, Society of Petroleum Engineers.

International Search Report and Written Opinion for related PCT application PCT/US2016/042017 dated Sep. 23, 2016.

* cited by examiner

SMART WATER FLOODING PROCESSES FOR INCREASING HYDROCARBON RECOVERY

PRIORITY CLAIM

This application is a non-provisional continuation-in-part application of U.S. application Ser. No. 15/209,597, filed Jul. 13, 2016, which itself claims priority to and the benefit of U.S. Prov. App. No. 62/193,951, filed Jul. 17, 2015, the entire disclosure of which is hereby expressly incorporated herein by reference.

FIELD

The present disclosure relates to methods, compositions, and techniques for enhancing the production of hydrocarbons such as crude oil from subterranean hydrocarbon bearing formations. In some embodiments, the disclosure relates to processes for evaluating enhanced oil recovery mechanisms in carbonate based reservoirs at both the rock-fluid and oil-water interfaces using spectroscopic and interfacial techniques. In further embodiments, the spectroscopic and interfacial techniques include microscopic, rheometric and tensiometric measurements. In preferred embodiments, the disclosed methods and techniques provide reservoir based details that allow for optimized "smart water" flooding practices and correspondingly higher oil recovery rates.

BACKGROUND

The use of enhanced oil recovery (EOR) processes has greatly benefited the oil and gas industry by increasing the production of problematic and underperforming hydrocarbon bearing wells and fields. The EOR processes used in modern oil and gas operations may include chemical, hydrochemical, thermal, fluid/superfluid and microbial based processes as well as the relatively recent plasma-pulse technology (PPT). Water injection (alternatively referred to as water flooding) has been widely used to increase the conductivity or flow of liquid hydrocarbons in subterranean reservoir treated using EOR techniques. The water source may be derived from freshwater, (for example, aquifers or surface water) as well as saltwater/brackish sources (for example, river/sea water mixtures).

The use of water flooding processes known as "smart water flooding" or simply "smart flooding" as described, e.g. in RezaeiDoust et al., *Energy Fuels* 23(9), 4479-4485 (2009); and Suman et al., *World Journal of Engineering and Technology* 2, 13-22 (2014), has found utility in recent EOR efforts. Smart flooding typically involves an ion (salt) based modification to the injectable water fraction that beneficially does not require costly chemical modifiers such as surfactants and nanomaterials. In addition, smart flooding is generally regarded as environmentally safe. However, the process of water flooding, particularly smart flooding, could be improved by developing a greater understanding of the physicochemical reservoir interactions occurring at the fluid-fluid (water-liquid hydrocarbon) and rock-fluid (reservoir-water-liquid hydrocarbon) interfaces. The need therefore exists for methods, compositions and techniques capable of improving water flooding and smart flooding as post-primary recovery processes for the recovery of crude oil and related liquid hydrocarbons.

SUMMARY OF THE INVENTION

The present disclosure provides for methods and techniques for enhancing the production of hydrocarbons such as crude oil from subterranean hydrocarbon bearing formations. In some embodiments, the disclosure relates to a method for increasing production in a liquid hydrocarbon reservoir formation comprising the steps of: (a) isolating a subterranean rock sample capable of bearing a liquid hydrocarbon; (b) combining a liquid hydrocarbon fraction with the subterranean rock sample under conditions capable of producing a first interface between the subterranean rock sample and the liquid hydrocarbon fraction, creating an interfacial liquid hydrocarbon fraction; (c) performing at least one spectroscopic measurement proximate the interfacial liquid hydrocarbon fraction and subterranean rock sample using one or more spectrometers; (d) combining a brine solution with the liquid hydrocarbon fraction under conditions capable of producing a second interface between the brine solution and the liquid hydrocarbon fraction; and (e) performing at least one spectroscopic measurement proximate the interfacial liquid hydrocarbon fraction and brine solution using one or more spectrometers.

In some embodiments, the spectroscopic measurement is selected from the group consisting of atomic force microscopy, Brewster angle microscopy, imaging ellipsometry, scanning electron microscopy, cryo-scanning electron microscopy, environmental scanning electron microscopy, transmission electron microscopy, surface force measurements, surface pressure measurements, surface potential measurements, confocal microscopy, molecular structural analyses, magnetic resonance measurements, monolayer molecular analyses, multilayer molecular analyses and combinations thereof. In further embodiments, the one or more spectrometers are selected from a scanning probe microscope, an atomic force microscope, a scanning force microscope, a rheometer, a tensiometer, a Langmuir-Blodgett trough, a nuclear magnetic resonance spectrometer, an absorption spectrometer, an emission spectrometer and combinations thereof.

In some embodiments, the one or more oil and water interfacial properties are selected from interfacial tension, surface pressure, surface potential, molecular structure, viscoelasticity, and combinations thereof. In further embodiments, the liquid hydrocarbon fraction is crude oil. In still further embodiments, the subterranean rock sample comprises carbonate. In additional embodiments, the method further comprises pressurizing the liquid hydrocarbon fraction and subterranean rock sample prior to step (c) and optionally increasing the temperature. In some embodiments, the method further comprises pressurizing the liquid hydrocarbon fraction, subterranean rock sample and brine fraction prior to step (e) and optionally increasing the temperature.

In some embodiments, the method further comprises introducing a primary oil recovery composition for recovering a liquid hydrocarbon fraction from the liquid hydrocarbon reservoir formation prior to step (a). In further embodiments, the method further comprises introducing a deflocculant into the liquid hydrocarbon fraction, subterranean rock sample and brine fraction prior to step (e). In still further embodiments, the deflocculant is selected from the group consisting of lignite, tannin, polycarbonate, polycarboxylate, polyacrylamide, sodium carboxymethyl cellulose, sodium citrate, sodium silicate, ammonium oxalate, sodium oxalate, gum arabic, humic acid resin, bentonite, and combinations thereof. In certain embodiments, the method further comprises introducing a proppant into the liquid hydrocarbon fraction, subterranean rock sample and brine fraction prior to step (e). In additional embodiments, the proppant is selected from the group consisting of sand, clay, bauxite, alumina and aluminosilicates and combinations thereof.

In some embodiments, the method further comprises introducing a dispersant into the liquid hydrocarbon fraction, subterranean rock sample and brine fraction prior to step (e). In further embodiments, the dispersant is selected from the group consisting of lignosulfate, polymethacrylate, hydroxypropyl methacrylate polyacrylamide, sodium vinyl sulfonate, sodium acrylamidomethylpropane sulfonate, phosphonobutane tricarboxylic acid, amino trimethylene phosphonic acid, hydroxyethylidene diphosphonic acid, sodium hydroxyethylidene diphosphonate, diethylenetriamine pentamethylene phosphonic acid and combinations thereof. In certain embodiments, the brine solution has a salt concentration in a range of about 1,000 parts per million to about 100,000 parts per million (ppm). In some embodiments, the salt is sodium chloride. In certain embodiments, the method further comprises combining one or more brine solutions with the liquid hydrocarbon and subterranean rock sample in step (b).

In some embodiments, the method further comprises introducing a subterranean rock sample in step (d). In alternative embodiments, sodium chloride may be depleted in accordance with some embodiments of the claimed method and/or may precipitate within the subterranean rock sample and/or spectrometer(s) used to perform one or more spectroscopic measurements. In further embodiments, sodium chloride may co-precipitate with one or more of calcium salts, magnesium salts, sulfate salts and combinations thereof within the subterranean rock sample and/or spectrometer(s) used to perform one or more spectroscopic measurements. In certain embodiments, embodiments of the disclosure increase the recovery of hydrocarbons from a subterranean hydrocarbon bearing reservoir formation by at least 10%, by at least 20%, by at least 50% or by at least 75%.

BRIEF DESCRIPTION OF THE DRAWINGS

So that the manner in which the features, advantages and objects of the invention, as well as others which will become apparent, are attained, and can be understood in more detail, a more particular description of the invention briefly summarized above may be had by reference to the embodiments thereof which are illustrated in the appended drawings that form a part of this specification. It is to be noted, however, that the drawings illustrate only a preferred embodiment of the invention and are therefore not to be considered limiting of the scope as the invention may admit to other equally effective embodiments. The present invention will be better understood on reading the following detailed description of non-limiting embodiments thereof, and on examining the accompanying drawings.

DETAILED DESCRIPTION

Figure 1:
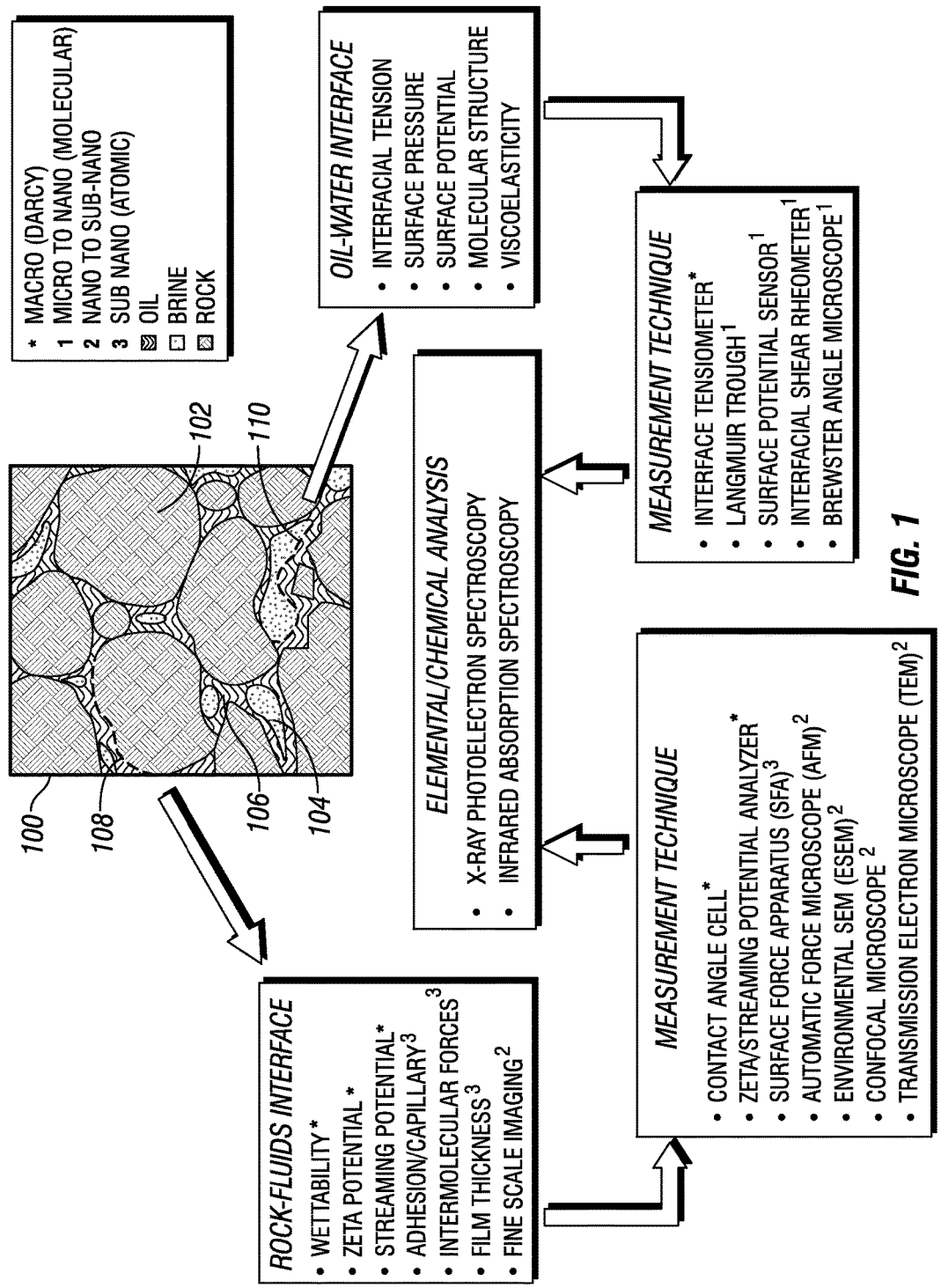
FIG. 1 shows a schematic of spectroscopic and interfacial analyses and techniques for enhancing oil recovery from a subterranean formation, for example a shale formation, in accordance with embodiments of the present disclosure.

Although the following detailed description contains specific details for illustrative purposes, the skilled artisan will appreciate that many examples, variations and alterations to the following details are within the scope and spirit of the invention. Accordingly, the exemplary embodiments of the disclosure described herein are set forth without any loss of generality, and without undue limitations, on the claimed invention.

As used herein, the terms "spectroscopy" and "spectroscopic technique" refer to manipulations and measurements using one or more spectrometers for the determination of properties associated with or attributable to improved water flooding techniques such as smart flooding techniques. In accordance with the present disclosure, spectrometers alone or in combination are capable of performing confocal microscopy, atomic force microscopy (AFM), Brewster angle microscopy, imaging ellipsometry, scanning electron microscopy (SEM) including environmental SEM (ESEM) and low temperature SEM (cryo-SEM), X-ray photoelectron spectroscopy (XPS), surface force measurements, surface pressure measurements, surface potential measurements, micro- and nano-tomography including X-ray microtomography, chromatography including ion chromatography, zeta potential analyses, molecular structural analyses including magnetic resonance measurements, monolayer and/or multilayer molecular analyses including molecular film analyses and combinations thereof.

Spectrometers and related instruments for use in embodiments of the present disclosure include but are not limited to scanning probe microscopes including atomic force microscopes, transmission electron microscopes, scanning force microscopes, confocal microscopes and Brewster angle microscopes, rheometers including interfacial shear rheometers (ISRs), tensiometers, Langmuir-Blodgett troughs, X-ray photoelectron spectrometers, nuclear magnetic resonance spectrometers, surface potential sensors, integrated thin film drainage apparatuses (ITFDAs), ZetaPALS and ZetaCAD spectrometers, chromatographs including ion chromatographs, absorption spectrometers and emission spectrometers capable of performing the manipulations and measurements disclosed herein.

The term "water flooding" refers to the use of water, either alone or supplemented with additional compositional and/or thermal agent(s) capable of enhancing oil recovery, in a wellbore, hydrocarbon bearing reservoir and/or rock formation (including porous and fractured rock formations) for the recovery of hydrocarbons. In some embodiments, the hydrocarbons are liquid hydrocarbons such as crude oil. In preferred embodiments, water flooding includes compositions and processes related to "smart water" flooding, as described, e.g. in RezaeiDoust et al., *Energy Fuels* 23(9), 4479-4485 (2009); and Suman et al., *World Journal of Engineering and Technology* 2, 13-22 (2014). In accordance with the present invention, smart water flooding compositions may comprise between about 1000 parts per million (ppm) to about 5000 ppm of a salt capable of enhancing oil recovery such as chloride ($Cl^-$) and sulfate ($SO_4^{2-}$) salts including sodium chloride (NaCl), calcium chloride ($CaCl_2$), magnesium chloride ($MgCl_2$), sodium sulfate ($Na_2SO_4$) and magnesium sulfate ($MgSO_4$).

As used herein, the term "rock-fluid interface" refers to the physiochemical and fluid properties related to and occurring at the liquid hydrocarbon/reservoir rock interface, the water/reservoir rock interface, and/or the liquid hydrocarbon/water/reservoir rock interface. While in no way limiting the scope of the present invention, these properties include surface pressure, surface potential, interfacial viscoelasticity, properties associated with interfacial microstructures, the visualization of rock-fluid interfacial interactions, wettability, properties associated with interfacial contact angles, zeta potential, streaming potential/current, adhesion and/or capillary forces, surficial thickness and/or intermolecular forces, The term "fluid-fluid interface" refers to the physiochemical and fluid properties related to and occurring at the liquid hydrocarbon/water interface. In some embodiments, the present disclosure relates to physiochemical and fluid properties at a crude oil/water interface. While in no way limiting the scope of the present invention, these properties include surface pressure, surface potential, interfacial viscoelasticity, film thickness, molecular orientation/packing and interfacial microstructures.

As used herein, the term "surfactant" refers to a compound capable of reducing the interfacial tension between two media, such as two liquids or a liquid and a solid. A surfactant in accordance with the present disclosure may refer to a cationic, anionic, zwitterionic or nonionic compound capable of behaving as a surfactant. In preferred embodiments, a surfactant for use in the present invention is an anionic compound such as a sulfonate or a sulfate compound.

The terms "sweep efficiency" and "volumetric sweep efficiency" refer to the efficacy of a process for increasing hydrocarbon recovery, including enhanced oil recovery (EOR) processes.

As used herein, "in situ" refers to an event or occurrence within a hydrocarbon reservoir including but not limited to methodologies, techniques and chemical reactions for enhancing hydrocarbon recovery. In preferred embodiments, the injection of a nanoencapsulated composition of the present disclosure into a hydrocarbon reservoir formation results in increased hydrocarbon production in the reservoir formation.

The present disclosure addresses problems associated with the recovery of liquid hydrocarbons from subterranean reservoir formations by analyzing the physicochemical properties associated with a hydrocarbon bearing formation. The spectroscopic measurements and analytical techniques described herein advantageously provide an enhanced understanding of the subterranean conditions associated with a hydrocarbon bearing reservoir for increasing hydrocarbon recovery and may be performed in the field to the extent possible as well as in in silico and laboratory simulations and systems. While in no way limiting the present invention to any particular theory or principle, in some embodiments the physicochemical properties determined using the methods and techniques described herein relate to fluid flow/transfer properties in porous and/or semi-porous compositions, for example subterranean rock formations, that may be interpreted using Darcy's law, which may be expressed as follows:

$$Q = (\kappa A/\mu)(\delta p/\delta x)$$

where Q is the flowrate of the fluid through the composition (typically expressed as volume per time), $\kappa$ is described as the "relative permeability" (typically expressed in units of permeability such as darcies, millidarcies or microdarcies, where a composition with a permeability of 1 darcy permits a flow of 1 $cm^3$/s of a fluid with viscosity 1 cP (1 mPa·s) under a pressure gradient of 1 atm/cm acting across an area of 1 $cm^2$), A is the cross-sectional area of the composition, and $(\delta p/\delta x)$ is the pressure change per unit length of the composition.

Figure 2:
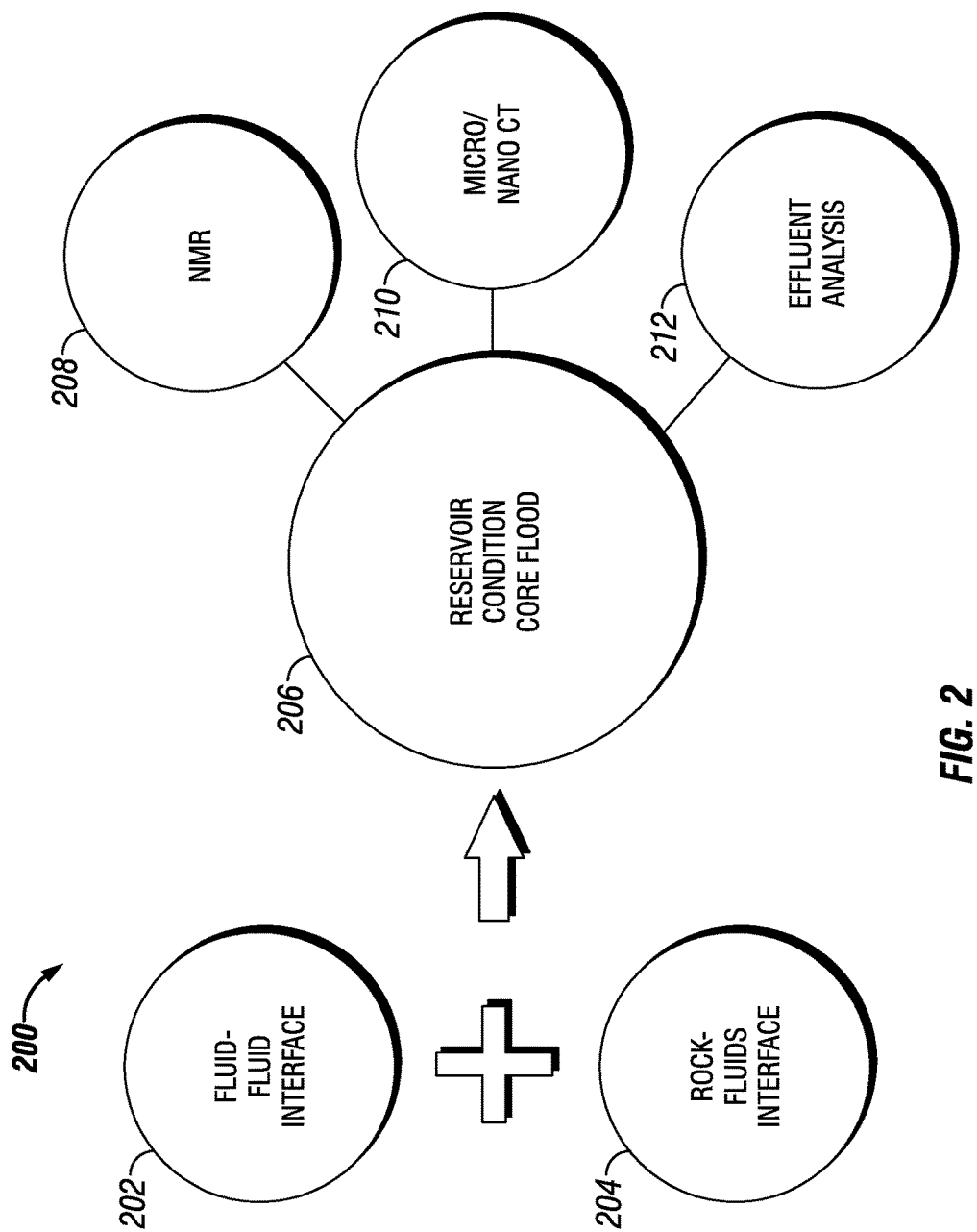
FIG. 2 shows an alternative schematic of spectroscopic and interfacial analyses and techniques for enhancing oil recovery from a subterranean shale formation in accordance with embodiments of the present disclosure.

The methods, compositions and techniques disclosed herein advantageously increase post-primary and/or post-secondary oil recovery in subterranean hydrocarbon bearing reservoirs, particularly in liquid hydrocarbon recovery processes for hydrocarbons such as crude oil. For instance, in accordance with some embodiments of the present disclosure, the schematics shown in FIGS. 1 and 2 depict complex interactions that may be observed in a subterranean hydrocarbon bearing reservoir including fluid-fluid interactions and rock-fluid interactions. These interfacial properties may be measured using a pendant drop or spinning drop interfacial tensiometer as well as by measuring the capillary action (such as the capillary rise or capillary motion) of the interfacial properties of the water and liquid hydrocarbon, as well as additional fluids of interest that may be capable of enhancing hydrocarbon recovery.

Referring now to FIG. 1, a schematic is shown of spectroscopic and interfacial analyses and techniques for enhancing oil recovery from a subterranean formation, for example a shale formation, in accordance with embodiments of the present disclosure. In a sample 100, rocks 102, brine solution 104, and oil 106 are mixed and intimately intermingled. Rocks 102 are rocks from a hydrocarbon bearing reservoir, for example a carbonate reservoir, sandstone reservoir, shale reservoir, or any other hydrocarbon bearing reservoir including tight formations. Brine solution 104 includes any type and any concentration of salt ions to be tested. Oil 106 includes any crude oil composition or other liquid hydrocarbon composition to be tested.

At a rock-fluids interface 108, rocks 102 are in interfacial contact with either or both of brine solution 104 and oil 106. Properties to be tested for at rock-fluid interface 108 include, but are not limited to, wettability, Zeta potential, streaming potential, adhesion and capillary forces, intermolecular forces, film thickness, and fine scale imaging. Measurement techniques for testing properties at rock-fluids interface 108 include, but are not limited to, contact angle cell, zeta/streaming potential analyzer, surface force apparatus, atomic force microscopy, environmental SEM, confocal microscopy, and transmission electron microscopy. Elemental and chemical analysis for testing at rock-fluids interface 108 include, but are not limited to, X-ray photoelectron spectroscopy and infrared absorption spectroscopy.

At oil-water interface 110, properties to be tested for include, but are not limited to interfacial tension, surface pressure, surface potential, molecular structure, and viscoelasticity. Measurement techniques for testing properties at oil-water interface 110 include, but are not limited to, interfacial tensiometer, Langmuir trough, surface potential sensor, interfacial shear rheometer, and Brewster angle microscopy. Elemental and chemical analysis for testing at oil-water interface 110 include, but are not limited to, X-ray photoelectron spectroscopy and infrared absorption spectroscopy. As shown in FIG. 1, properties and measurement techniques are correlated to the general scale at which the measurements and properties are applicable, such as on the macro-scale (Darcy) (*), micro to nano scale (molecular) (1), nano to sub-nano scale (2), and sub-nano (atomic) scale (3).

Referring now to FIG. 2, a schematic is shown of spectroscopic and interfacial analyses and techniques for enhancing oil recovery from a subterranean shale formation in accordance with embodiments of the present disclosure. In an example method 200, at step 202 a fluid-fluid interface is created, such as, for example, between water and oil, and at step 204 a rock-fluids interface is created, optionally by adding rock to a mixture of fluids, such as oil and water. At step 206, reservoir conditions at core flooding are simulated, for example optionally with elevated pressure and temperature. At step 208, NMR can be carried out on a sample. At step 210 micro or nano computed tomography can be carried out on a sample. At step 212 effluent analysis can be carried out on a sample.

In addition, the surface pressure and surface potential properties of the fluid-rock interfaces and fluid-fluid interfaces relevant to the present technology may be determined using instruments such as a Langmuir trough and a surface potential sensor (alternatively referred to as a surface electric potential sensor). The interfacial viscoelasticity of fluid-fluid interfaces in accordance with the present disclosure, including liquid hydrocarbon/water interfacial properties, may be determined using an interfacial shear rheometer (ISR), while properties associated with interfacial microstructures at the fluid-rock interface may be evaluated with a Brewster angle microscope, including microscopes capable of performing Langmuir and Langmuir-Blodgett measurements on compositions relevant to the present invention, and/or an imaging ellipsometer.

In accordance with certain embodiments of the present disclosure, the determination and visualization of rock-fluid interfacial interactions may further include measurements directed to wettability and contact angles at the fluid rock interface and include static and dynamic contact angle measurements determined using optical tensiometry and/or force tensiometry. The zeta potential of a fluid or fluids at a fluid-rock interface in accordance with the present invention may be determined or simulated using ZetaPALS, or ZetaCAD instruments, while the streaming current/potential of a surface at the fluid-rock interface, including the zeta potential, may be determined using an electrokinetic analyzer or a ZetaCAD instrument.

In some embodiments, the adhesion and/or capillary forces associated with fluid-rock interfacial properties may be investigated using atomic force microscopy (AFM) and integrated thin film drainage apparatus (ITFDA), while surficial thickness and/or intermolecular forces may be evaluated using surface force apparatuses (SFAs) including the use of an extended surface force apparatus (eSFA). In addition, high resolution images detailing the interactions occurring at the fluid-rock and fluid-fluid interfaces may be investigated using AFM, confocal microscopy, ESEM, cryo-SEM and transmission electron microscopy (TEM). The properties related to the chemical compositions at the rock and fluid interfaces, including elemental analyses of the rock, water and/or liquid hydrocarbon(s) of interest, may be determined using X-ray photoelectron spectroscopy (XPS), while analyses of rock, water and/or liquid hydrocarbon chemical groups contributing to fluid-rock and fluid-fluid properties, such as the functional groups present in crude oil, may be investigated using infrared spectroscopy.

Core flood testing, including reservoir conditions core flood testing and computer controlled core flood testing, may be used to evaluate pressure effects and properties related to enhanced oil recovery (EOR) processes in accordance with the present disclosure. In addition, the evaluation and investigation of properties related to frontal advancement (including chemical assisted frontal advancement such as polymer- and surfactant-assisted frontal advancement), oil bank saturation and fluid distribution may be determined via micro-computed tomography (micro-CT), nano-CT or X-ray tomography including high-resolution X-ray tomography. The pore connectivity and ion related properties at the rock-fluid interfaces described herein may be investigated using NMR, while effluent analyses of water species relevant to fluid-fluid and rock-fluid interfaces may be evaluated using scanning analyzers as well as ion chromatography.

The methods, compositions and techniques of the present disclosure may beneficially be supplemented with one or more compositional and/or thermal agents capable of increasing liquid hydrocarbon recovery from a subterranean reservoir formation. For instance, the methods, compositions and techniques of the present invention may be supplemented with additional compositions for increasing hydrocarbon recovery. In addition, the methods and techniques of the present disclosure may increase liquid hydrocarbon flow and sweep efficiency and therefore increase liquid hydrocarbon recovery.

These compositions include but are not limited to surfactants such as hydrocarbon based surfactants, sulfonate based surfactants, sulfate based surfactants and phosphate based surfactants; deflocculants such as lignite, tannin, polycarbonate, polycarboxylate, polyacrylamide, sodium carboxymethyl cellulose, sodium citrate, sodium silicate, ammonium oxalate, sodium oxalate, gum arabic, humic acid resin and bentonite; proppants such as sand, clay, bauxite, alumina and aluminosilicates; dispersants such as lignosulfate, polymethacrylate, hydroxypropyl methacrylate polyacrylamide, sodium vinyl sulfonate, sodium acrylamidomethylpropane sulfonate, phosphonobutane tricarboxylic acid, amino trimethylene phosphonic acid, hydroxyethylidene diphosphonic acid, sodium hydroxyethylidene diphosphonate and diethylenetriamine pentamethylene phosphonic acid; and combinations thereof.

Example

The following example is included to demonstrate preferred embodiments of the invention. It should be appreciated by those of skill in the art that the techniques and compositions disclosed in the example which follows represent techniques and compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or a similar result without departing from the spirit and scope of the invention.

Example 1

In a non-limiting example, a carbonate reservoir rock sample optionally containing crude oil is isolated and placed in a sample holder capable of containing: 1) water and/or brine solutions; and/or 2) crude oil. A fraction of crude oil is introduced into the sample holder and allowed to contact the carbonate reservoir rock sample, optionally in the presence of a brine solution, under conditions appropriate for forming a rock-crude oil interface. The resulting rock-crude oil sample is evaluated for one or more of wettability, film stability, surface potential and intermolecular surficial properties using one or more of AFM, a surface force apparatus (SFA) and/or an integrated thin film drainage apparatus (ITFDA). The sample is further subjected to AFM, ESEM and/or confocal microscopy for evaluating the physical appearance of the surficial interface. Finally, the sample is evaluated at the molecular level using XPS and/or infrared absorption spectroscopy for determining, for example, the identity and concentration of chemical species formed at or around the rock-crude oil interface.

The rock-crude oil containing sample holder is further supplemented with brine under conditions capable of forming a brine-crude oil interface in the presence of a carbonate reservoir rock sample. The resulting rock-crude oil-brine sample is evaluated for interfacial tension, surface potential and pressure, as well as viscoelasticity at the brine-crude oil interface. The sample is further investigated using a Langmuir trough, Brewster angle microscopy and imaging ellipsometry. Finally, the rock-crude oil-brine sample is evaluated at the molecular level using XPS and/or infrared absorption spectroscopy for determining, for example, the identity and concentration of chemical species formed at or around the brine-crude oil interface.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural references, unless the context clearly dictates otherwise.

"Optional" or "optionally" means that the subsequently described component may or may not be present or the event or circumstances may or may not occur. The description includes instances where the component is present and instances where it is not present, and instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

What is claimed is:

1. A method for measuring liquid-rock and liquid-liquid interfaces, the method comprising the steps of:
    performing at least one measurement technique proximate a subterranean rock sample and an interfacial liquid hydrocarbon fraction, where a liquid hydrocarbon fraction and the subterranean rock sample are combined to exhibit a first interface between the liquid hydrocarbon fraction and the subterranean rock sample, producing the interfacial liquid hydrocarbon fraction; and
    performing at least one measurement technique proximate the interfacial liquid hydrocarbon fraction and a brine solution, where the liquid hydrocarbon fraction and the brine solution are combined to exhibit a second interface between the liquid hydrocarbon fraction and the brine solution, and where the measurement techniques result in measurements of the interfacial liquid hydrocarbon fraction at macro, micro to nano, nano to sub-nano, and sub-nano scales, and result in measurements of the second interface at macro and micro to nano scales.

2. The method of claim 1, where at least one measurement technique is selected from the group consisting of: atomic force microscopy, Brewster angle microscopy, imaging ellipsometry, scanning electron microscopy, cryo-scanning electron microscopy, environmental scanning electron microscopy, transmission electron microscopy, surface force measurements, surface pressure measurements, surface potential measurements, confocal microscopy, molecular structural analyses, magnetic resonance measurements, monolayer molecular analyses, multilayer molecular analyses, and combinations thereof.

3. The method of claim 1, where at least one measurement technique includes the use of at least one device selected from the group consisting of: a scanning probe microscope, an atomic force microscope, a scanning force microscope, a rheometer, a tensiometer, a Langmuir-Blodgett trough, a nuclear magnetic resonance spectrometer, an absorption spectrometer, an emission spectrometer, an integrated thin film drainage apparatus, and combinations thereof.

4. The method of claim 1, where the at least one measurement technique proximate the interfacial liquid hydrocarbon fraction and the brine solution is applied to analyze a property selected from the group consisting of: interfacial tension, surface pressure, surface potential, molecular structure, viscoelasticity, and combinations thereof.

5. The method of claim 1, further comprising the step of:
    performing at least one elemental and chemical analysis proximate the subterranean rock sample and the interfacial liquid hydrocarbon fraction.

6. The method of claim 5, where the at least one elemental and chemical analysis is selected from the group consisting of: X-ray photoelectron spectroscopy, infrared absorption spectroscopy, and combinations thereof.

7. The method of claim 5, where the at least one elemental and chemical analysis includes the use of at least one device selected from the group consisting of: an X-ray photoelectron spectrometer, an absorption spectrometer, an emission spectrometer, and combinations thereof.

8. The method of claim 5, where the at least one elemental and chemical analysis proximate the subterranean rock sample and the interfacial liquid hydrocarbon fraction is applied to analyze a property selected from the group consisting of: chemical compositions, concentrations of chemical compositions, functional groups, and combinations thereof.

9. The method of claim 1, further comprising the step of:
    performing at least one elemental and chemical analysis proximate the interfacial liquid hydrocarbon fraction and the brine solution.

10. The method of claim 9, where the at least one elemental and chemical analysis is selected from the group consisting of: X-ray photoelectron spectroscopy, infrared absorption spectroscopy, and combinations thereof.

11. The method of claim 9, where the at least one elemental and chemical analysis includes the use of at least one device selected from the group consisting of: an X-ray photoelectron spectrometer, an absorption spectrometer, an emission spectrometer, and combinations thereof.

12. The method of claim 9, where the at least one elemental and chemical analysis proximate the interfacial liquid hydrocarbon fraction and the brine solution is applied to analyze a property selected from the group consisting of: chemical compositions, concentrations of chemical compositions, functional groups, and combinations thereof.

13. The method of claim 1, where the liquid hydrocarbon fraction comprises crude oil.

14. The method of claim 1, where the subterranean rock sample comprises carbonate.

15. The method of claim 1, further comprising the step of:
    pressurizing the liquid hydrocarbon fraction and the subterranean rock sample.

16. The method of claim 1, further comprising the step of:
    pressurizing the liquid hydrocarbon fraction, the subterranean rock sample, and the brine solution at an elevated temperature above room temperature.

17. The method of claim 1, further comprising the step of:
introducing a primary oil recovery composition including a brine with at least one component selected from the group consisting of: $CO_2$, a chemical solvent, a polymeric, surfactant, and nanoparticles, for recovering the liquid hydrocarbon fraction from a liquid hydrocarbon reservoir formation.

18. The method of claim 1, further comprising the step of:
introducing into the liquid hydrocarbon fraction, the subterranean rock sample, and the brine solution one composition selected from the group consisting of: a deflocculant, a proppant, a dispersant, and combinations thereof.

19. The method of claim 1, where the brine solution has a salt concentration in a range of 1,000 parts per million to 100,000 parts per million.

20. The method of claim 1, where the brine solution comprises at least one salt selected from the group consisting of: chloride salts, sulfate salts, sodium salts, calcium salts, magnesium salts, and combinations thereof.

* * * * *